United States Patent
Hochleitner et al.

(10) Patent No.: US 9,707,523 B2
(45) Date of Patent: Jul. 18, 2017

(54) MEMBRANE FILTER INCLUDING BILE ACID AND A METHOD OF MANUFACTURING THE SAME

(71) Applicant: WHATMAN GMBH, Dassel (DE)

(72) Inventors: Klaus Hochleitner, Dassel (DE); Suzana Kiel, Dassel (DE)

(73) Assignee: Whatman GmbH, Dassel (DE)

( * ) Notice: Subject to any disclaimer, the term of this patent is extended or adjusted under 35 U.S.C. 154(b) by 348 days.

(21) Appl. No.: 14/380,488

(22) PCT Filed: Feb. 22, 2013

(86) PCT No.: PCT/EP2013/053620
§ 371 (c)(1),
(2) Date: Aug. 22, 2014

(87) PCT Pub. No.: WO2013/127709
PCT Pub. Date: Sep. 6, 2013

(65) Prior Publication Data
US 2015/0027945 A1    Jan. 29, 2015

(30) Foreign Application Priority Data

Feb. 29, 2012  (GB) .................................. 1203546.5

(51) Int. Cl.
*B01D 71/12* (2006.01)
*B01D 71/16* (2006.01)
(Continued)

(52) U.S. Cl.
CPC ......... *B01D 71/12* (2013.01); *B01D 67/0002* (2013.01); *B01D 67/0086* (2013.01);
(Continued)

(58) Field of Classification Search
None
See application file for complete search history.

(56) References Cited

U.S. PATENT DOCUMENTS 3,026,571 A    3/1962  Maier
7,020,355 B2*  3/2006  Lahann .............. B01D 15/3861
                                                      365/151

(Continued)

FOREIGN PATENT DOCUMENTS

DE    197 40 770    3/1999
WO    WO 00/77242   12/2000
(Continued)

OTHER PUBLICATIONS

Chinese Office Action and Search Report for CN Application No. 201380011604.X mailed Aug. 20, 2015 (14 pages).

*Primary Examiner* — Krishnan S Menon
(74) *Attorney, Agent, or Firm* — Eversheds Sutherland (US) LLP

(57) ABSTRACT

A membrane filter 26 is disclosed comprising cellulous material 23 allowing the transition of fluid therethrough, and, in a substantially dry state, said membrane comprising also a salt of deoxycholic acid. Optionally, the air side of the membrane (the side facing away from the screen or belt used to manufacture the membrane) faces the sample fluid during use of the membrane. A method of manufacture of the membrane material is disclosed also, employing deoxycholic acid as a surfactant, to improve the recovery rate of the membrane filter in use.

14 Claims, 1 Drawing Sheet

Figure 1:
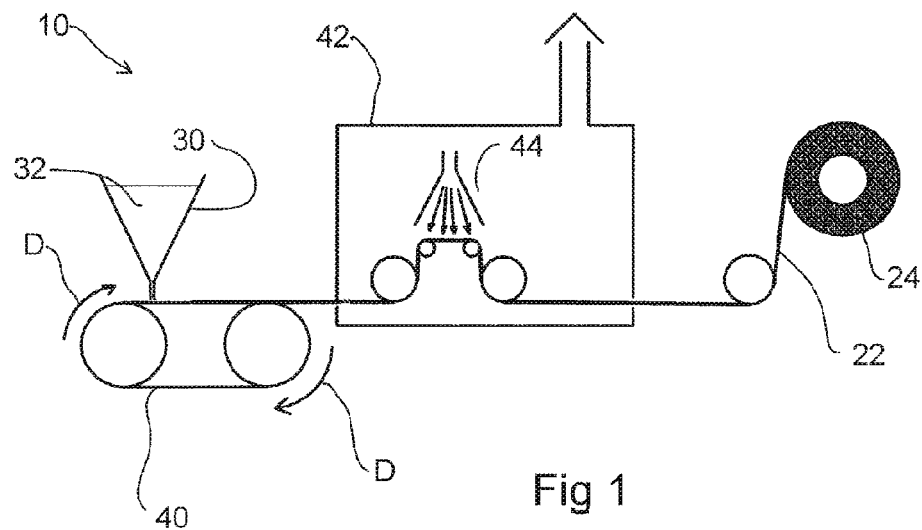

(51) Int. Cl.
  *B01D 71/20* (2006.01)
  *B01D 67/00* (2006.01)
  *B01D 69/02* (2006.01)
  *C12Q 1/24* (2006.01)
  *G01N 1/40* (2006.01)

(52) U.S. Cl.
  CPC ..... *B01D 67/0088* (2013.01); *B01D 67/0095* (2013.01); *B01D 69/02* (2013.01); *B01D 71/16* (2013.01); *B01D 71/20* (2013.01); *C12Q 1/24* (2013.01); *B01D 2325/08* (2013.01); *B01D 2325/12* (2013.01); *G01N 2001/4088* (2013.01)

(56) References Cited

U.S. PATENT DOCUMENTS

| | | | |
|---|---|---|---|
| 7,910,002 | B2 | 3/2011 | Johnson et al. |
| 2004/0256749 | A1 | 12/2004 | Chaubal et al. |
| 2013/0089923 | A1* | 4/2013 | Moeller ............. B82Y 5/00 435/289.1 |

FOREIGN PATENT DOCUMENTS

| WO | WO 03/090924 | 11/2003 |
|---|---|---|
| WO | WO 2012/037101 | 3/2012 |

* cited by examiner

MEMBRANE FILTER INCLUDING BILE ACID AND A METHOD OF MANUFACTURING THE SAME

CROSS-REFERENCE TO RELATED APPLICATIONS

This application is a filing under 35U.S.C. 371of international application number PCT/EP2013/053620, filed Feb. 22, 2013, published on Sep. 6, 2013 as WO 2013/127709, which claims priority to application number 1203546.5filed in Great Britain on Feb. 29, 2012.

The invention relates to a membrane filter, and a method of manufacture the membrane filter. The invention also relates to a method for the microbiological analysis of fluid samples including filtration using the membrane filter of the invention. In this application the term fluid or fluids, includes liquids, gases, aerosols, and fluidised solids.

Conventionally, microbiological analysis of liquids, such as beverages, drinking water, treated waste water, or river water, involves filtering a sample of the liquid to be analysed, optionally using differential pressure across the filter, to retain any microorganisms in the filter. The filter is then laid in a Petri dish with a nutrient medium and stored in an incubator for a predetermined time at an elevated temperature. The nutrient medium stimulates the growth of any microorganisms present on the filter.

After the predetermined time, any microorganisms caught in the filter should have grown into colonies which are visible to the naked eye, and thus can be counted, to quantify the level of contamination of the liquid sample.

During manufacture, known membrane material is formed by a casting procedure that involves dissolving of the membrane raw materials in organic solvents, containing also a pore forming substance, pouring this solution (the "casting mix") onto a solid carrier belt, moving this belt through a closed cabinet in which the solvents are evaporated under controlled conditions until the membrane raw materials precipitate to form the final membrane structure. The final membrane contains a surfactant that may either be a part of the raw material solution discussed above, or may be coated onto the membrane in a separate manufacturing step. The formed membrane is lifted off the belt in a conventional way. One such manufacturing technique is shown in GB903270. Known membrane filters are then cut to shape and a grid is printed on their surface to aid manual counting of the microorganism colonies. The membrane, manufactured in such a way, has two sides; a first side closest to the belt; the belt side, and a second side opposite the first side; the air side.

There are a number of problems using this technique. A significant problem is that the filter material needs to be produced to precise standards; for example the pore size is critical. To aid this consistent manufacture, a surfactant called Statexan K1, a sodium alkylsulfonate with a mean chain length of 15 C-Atoms, has been used by the Applicant in the casting mix to provide consistent quality. However, the residue of this surfactant has a detrimental effect on the growth of the microorganisms following the filtering step. Without the surfactant the quality of the filter will be lower.

Another problem is that not all microorganisms are retained by the filter, because the filter has to have a pore size which allows fluid, for example a viscous fluid food, to pass reasonably quickly, but that pores size will not catch, for example, all bacteria or mould spores which are inherently small in size. The ability to detect microorganisms; i.e. catching, retaining and growing the microorganisms, is known as the recovery rate, and is typically given as a percentage, where 100% is perfect recovery of all microorganisms.

Embodiments of the invention address, at least, the above problems.

According to the invention, there is provided a membrane filter formed from a fluid casting mix, wherein a bile acid or bile acid derivative is introduced during the manufacture of said membrane, and once dried the membrane comprising a membrane material for retaining microorganisms and also a residual salt of said bile acid or bile acid derivative.

Thus, when a bile acid such as deoxycholic acid is used as a surfactant during the manufacturing of the membrane filter, a salt residue is formed from that surfactant.

Deoxycholic acid, also known as deoxycholate, cholanoic acid, and $3\alpha,12\alpha$-dihydroxy-$5\beta$-cholanate, and is a secondary bile acid. Through experimentation, the surfactant salt residue was shown to exhibit low interference with microbial growth, thereby increasing the overall recovery rate.

In an embodiment, the deoxycholic acid is $7\alpha$-deoxycholic acid.

In an embodiment the air side faces directly the sample fluid during use of the membrane filter, and the belt side faces away from the fluid in use.

It has been found that this air side provides a better growth environment for microorganisms, particularly in conjunction with the relatively mild nature of the deoxycholic acid residue remaining after filtering. The result is that the air side filtration and surfactant specified provide a membrane filter with a recovery rate of 90% or better.

In an embodiment, the membrane filter has a dry thickness of about 130 to about 140 μm, preferably around 135 μm.

In an embodiment the membrane filter is composed substantially of a mixture of cellulose acetate and cellulose nitrate.

In an embodiment the membrane filter has a grid pattern printed on one side, preferably the air side.

The invention also provides a method of manufacturing a membrane filter, the method including the steps of:
  a) preparing a casting mix, including dissolved cellulosic material;
  b) introducing a surfactant to the casting fluid including a bile acid or bile acid derivative for example deoxycholic acid; and
  c) casting the mix on a surface to form a membrane material which includes said surfactant.

In an embodiment, the method further includes the steps of:
  d) drying the web; and
  e) brushing the air side of the web, i.e. the side opposite the casting surface.

In an embodiment the method further includes the steps of:
  f) printing a grid pattern on the air side; and
  g) optionally, cutting the membrane material to shape for use.

In an embodiment, the deoxycholic acid concentration in the casting mix is less than 0.06% (w/w), and is preferably 0.02 to 0.04% (w/w), and more preferably 0.03% (w/w).

The invention extends to use of a membrane filter according to the first aspect, or use of the membrane filter prepared according to the second aspect for the microbiological analysis of fluid samples including filtering said samples using the membrane filter and culturing the retainate of the filter.

Figure 2:
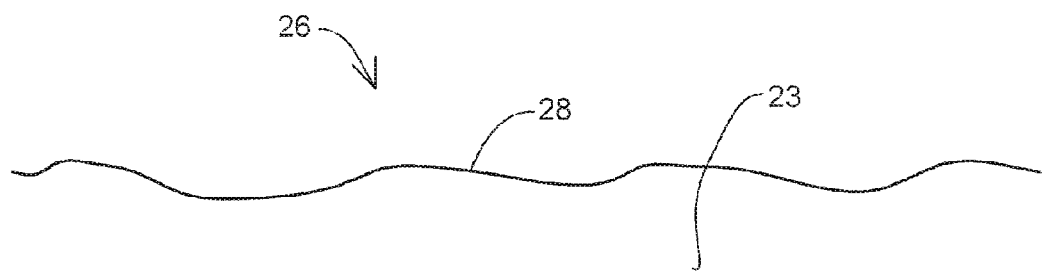

The invention can be put into effect in numerous ways, one embodiment only being described and illustrated, with reference to the attached drawings, wherein:

FIG. 1 shows apparatus for manufacturing a membrane filter according to the invention; and FIG. 2 shows an enlarged sectional view of a membrane filter according to the invention.

Referring to FIG. 1, a schematic representation of apparatus 10 for manufacturing a membrane filter web 20 is shown. A vat 30 includes a so called casting mix 32 of a solvent, cellulose acetate, cellulose nitrate, and deoxycholic acid which acts as a surfactant. In this deoxycholic acid comprises around 0.03% (w/w) of the casting mix.

A continuous belt 40 travels in the direction of arrows D, and picks up the casting mix 32 poured from the vat 30 to form a continuous film. The web material is, heated at station 44, within a ventilated cabinet 42, to produce a porous membrane material resulting from evaporation of the solvent. Brushing of the side of the membrane material which faces away from the belt can be carried out later, to provide a more readily printable surface.

The now dried web 22 is peeled off the belt 40 and rolled onto a storage roll 24. Membrane material on the storage roll 24 can be cut or punched to make individual membranes (26 FIG. 2). The membranes are printed with a grid pattern to aid quantification of microbiological material in use.

Referring to FIG. 2, a section through a membrane 26 is shown comprising a mixture 23 of cellulose acetate and cellulose nitrate formed to be porous membrane. The membrane 26 will contain also salts which are a residue from the deoxycholic acid used in the casting process described above.

The membrane is about 135 μm in thickness and has a pore size of about 0.1 to 12 μm, preferably 0.1 to 1 μm.

One side 21, of the membrane is the side which faced the belt 40 during production, whereas the other side 28, the so-called air side, faced away from the belt 40 during production. Under a microscope it is possible to see that the air side has a rougher surface which appears to catch and retain microorganisms better than the belt side. It was found that using the air side as the fluid facing side improved the recovery rate by around 10% where deoxycholic acid surfactant was employed.

In experiments other surfactants were used but they did not perform as well as deoxycholic acid. For example:

| Surfactant % (w/w) in casting mix | Recovery of E. coli (%) according to Standard Method 9222D (belt side) | Retention of E. coli (%) according to Standard Method DIN 58355, part 3 (belt side) |
| --- | --- | --- |
| 0.06% Statexan K1 | 67 | 100 |
| 0.01% Statexan K1 | 74 | 100 |
| 0.01% Deoxycholic acid | 78 | 100 |
| *0.03% Deoxycholic acid | 82 | 100 |
| 0.01% Tween 20 | 74 | 100 |

For the 9222D method, the table above shows that the recovery rate of membranes using Statexan improved with lower concentrations of that surfactant, as would be expected, because there would be lower concentrations of surfactant residue in the finished membrane and therefore less anti-microbial activity in the membrane in use. Problems with forming the membrane web were encountered with use of Tween 20 as a surfactant in higher concentrations than 0.01%, so that was dismissed. Contrary to logical thoughts, increasing levels of deoxycholic acid improved both the web quality and the recovery rate of membranes produced using that casting mix. It was found that 0.03% was an optimum value, but that 0.02% to 0.04% was considered to give satisfactory results, and less than 0.06% was considered to be workable. Increasing levels of Deoxycholic acid up to around 0.03% improved recovery rates, which is opposite to the results found for increasing Statexan. Thus the recovery rates and ease of manufacture of the membrane web are unpredictable when selecting the surfactant to be used and its concentration.

For method DIN 58355, the table above shows that the retention of bacteria in the membranes was not influenced by the surfactant and there were no bacteria found in the filtrate of bacterial solutions filtered through the membranes. Thus for this test methodology, the choice of surfactant used has no bearing on the retention efficiency of the membrane. Thus, again, the effects of the choice of surfactant employed are not predictable.

Selection of the air side as mentioned above improved the recovery rate of membrane of the invention still further by an additional 10%, bringing the overall recovery rate of the preferred membrane (* in the table above) to around 92%.

The membrane is used in a manner described above which is conventional. In another use, the membrane filter may retain microorganisms on its surface without sample fluids passing completely through the membrane.

Although one embodiment only has been described, it would be readily apparent to the skilled addressee that modifications, additions and omissions are possible within the scope of the invention. For example, cellulosic based membrane filters are discussed, but other base materials could be employed for example other polymers such as PVDF or polysulfones. Other constituents may be included in the casting mix, for example binders, or microbial staining reagents, or dyes.

A printed grid pattern is preferred but that is not essential. The membrane could be unprinted, or printed with another pattern, for example a hexagonal pattern. Other means of marking the membrane besides printing could be employed. The continuous manufacturing technique described could be replaced by manual production where a screen is used to cast the membrane material, and thereby form a matrix of material rather than a continuous web as described.

The invention claimed is:

1. A membrane filter comprising:
   a membrane material for retaining microorganisms having an air-side surface and a belt-side surface, the air-side surface being rougher than the belt-side surface; and
   a bile acid or bile acid derivative residual salt dispersed throughout the membrane material and non-covalently associated therewith.

2. The membrane filter of claim 1, wherein a salt residue of 7α-deoxycholic acid is dispersed throughout the membrane material.

3. The membrane filter of claim 1, wherein the membrane filter has a recovery rate defined by method 9222D of 90% or better.

4. The membrane filter of claim 1, wherein the membrane filter has a dry thickness of about 130 to about 140 μm.

5. The membrane filter of claim 1, wherein the membrane material is composed substantially of a mixture of cellulose acetate and cellulose nitrate.

6. The membrane filter of claim 1, wherein the membrane filter includes a surface pattern.

7. A method of manufacturing a membrane filter material, the method including the steps of:
   a) preparing a casting mix, including cellulosic polymers, preferably cellulose nitrate and cellulose acetate dissolved in at least one organic solvent;
   b) introducing a surfactant in the casting mix including a bile acid or bile acid derivative; and
   c) casting the mix on a carrier belt to form the membrane filter material by controlled evaporation of the solvent(s), leaving the surfactant in the membrane filter material.

8. The method of manufacturing the membrane filter material of claim 7, the method further including the steps of:
   d) drying the membrane material; and
   e) brushing the side of the membrane material opposite the belt side of the material.

9. The method of manufacturing the membrane filter material of claim 8, the method further including the steps of:
   f) printing a grid pattern on the air side; and
   g) optionally, cutting the material to shape for use.

10. The method of manufacturing the membrane filter material of claim 7, wherein the bile acid or bile acid derivative is deoxycholic acid, in a concentration in the casting liquid is less than 0.06% (w/w).

11. The method of manufacturing the membrane filter of claim 7, wherein the casting liquid is 0.02 to 0.04% (w/w).

12. The method of manufacturing the membrane filter of claim 7, wherein the casting liquid is about 0.03% (w/w).

13. The membrane filter of claim 1, wherein the membrane filter has a dry thickness of about 135 µm.

14. The membrane filter of claim 6, wherein the surface pattern is a grid pattern printed on the air-side surface.

* * * * *